(12) United States Patent
Sweitzer et al.

(10) Patent No.: US 12,256,963 B2
(45) Date of Patent: Mar. 25, 2025

(54) DUAL ROD IMPLANT CUTTER

(71) Applicant: Shukla Medical, St. Petersburg, FL (US)

(72) Inventors: Zachary Robert Sweitzer, Keyport, NJ (US); Brian Joseph Servedio, St. Petersburg, FL (US)

(73) Assignee: Shukla Medical, St. Petersburg, FL (US)

( * ) Notice: Subject to any disclaimer, the term of this patent is extended or adjusted under 35 U.S.C. 154(b) by 981 days.

(21) Appl. No.: 17/324,616

(22) Filed: May 19, 2021

(65) Prior Publication Data

US 2021/0361326 A1 Nov. 25, 2021

Related U.S. Application Data

(60) Provisional application No. 63/026,972, filed on May 19, 2020.

(51) Int. Cl.
*A61B 17/56* (2006.01)
*A61B 17/17* (2006.01)
*A61B 17/70* (2006.01)
*A61B 17/00* (2006.01)
*A61B 17/16* (2006.01)

(52) U.S. Cl.
CPC ...... *A61B 17/7082* (2013.01); *A61B 17/1757* (2013.01); *A61B 2017/00477* (2013.01); *A61B 2017/1602* (2013.01)

(58) Field of Classification Search
CPC ............ A61B 17/7082; A61B 17/1757; A61B 2017/00477; A61B 2017/1602; B23D 51/02; B23D 59/006; B23D 49/002; B28D 7/02; B28D 1/045

USPC ....... 606/53, 79, 279; 83/24, 78, 100, 471.3, 83/478, 581, 745, 746
See application file for complete search history.

(56) References Cited

U.S. PATENT DOCUMENTS

| 5,988,027 A | * | 11/1999 | Lenox | ...................... B25G 1/04 83/699.61 |
| 9,427,274 B1 | | 8/2016 | McVean et al. | |
| 11,950,818 B2 | * | 4/2024 | Servedio | ............ A61B 17/8863 |
| 2009/0264887 A1 | * | 10/2009 | Beale | ................. A61B 17/8863 606/80 |
| 2016/0346027 A1 | | 12/2016 | Rouge et al. | |

(Continued)

FOREIGN PATENT DOCUMENTS

EP 3210555 A1 8/2017

OTHER PUBLICATIONS

International Search Report for International Application No. PCT/US2021/033135, issued Sep. 15, 2021.

(Continued)

*Primary Examiner* — Tessa M Matthews
*Assistant Examiner* — David C Comstock
(74) *Attorney, Agent, or Firm* — Kim IP Law Group LLC

(57) ABSTRACT

A cutter for cutting an implant is provided. The cutter includes a gearbox; a primary milling bit, a secondary milling bit and a lead screw operatively coupled to the gearbox; an input coupling coupled rigidly to the primary milling bit; and an implant coupler coupled rigidly to the lead screw, wherein the gearbox is operable to translate with respect to the lead screw and to drive the secondary milling bit in response to a driving force applied to the input coupling.

24 Claims, 19 Drawing Sheets

(56) References Cited

U.S. PATENT DOCUMENTS

2017/0151006 A1    6/2017  Fischer et al.
2017/0245907 A1*  8/2017  Sharifi-Mehr ..... B23Q 11/0071

OTHER PUBLICATIONS

Written Opinion of the International Searching Authority for International Application No. PCT/US2021/033135, issued Sep. 15, 2021.
IP Australia, Office Action in counterpart application No. 2021277283 issued on Oct. 10, 2023.
European Patent Office, Examination Report in counterpart application No. 21739468.3 issued on Jun. 4, 2024.
Chinese National Intellectual Property Office, Office Action in counterpart application No. 2021800295650 issued on Jul. 1, 2024.

* cited by examiner

DUAL ROD IMPLANT CUTTER

CROSS REFERENCE TO RELATED APPLICATIONS

The present application claims the benefit of U.S. Provisional Patent Application No. 63/026,972 filed on May 19, 2020 and entitled "Spine Rod Cutter," the entire disclosure of which is expressly incorporated herein by reference.

BACKGROUND OF THE INVENTION

Various types of surgeries involve the placement of implants, such as spine rods, within patients. There is often a need or desire to adjust the length of a spine rod after it has been implanted, as precise determination of the exact length of the spine rod can often be difficult or impossible to predict prior to surgery. Standard protocol for certain surgical procedures may also require cutting a spine rod after implantation to best provide an ideal, customized length for an individual patient. To adjust the length, the spine rod may be removed from the patient, cut to the desired length off-site and re-implanted within the patient at a later time. However, this procedure is time-consuming, costly, and may require patients to undergo multiple surgeries. Typical spine rod cutters are also difficult to align and use, often requiring a user to devote substantial attention to ensuring that the cutter remains aligned and engaged with the spine rod during a cutting operation. There is, thus, a need for an efficient and effective implant cutter that may be employed in-situ.

Additionally, during a revision surgery in which the spine rod is removed, it can be to the surgeon's advantage to cut the rod in order to facilitate easier removal. Also, the surgeon may not have the correct drivers to unscrew the locking caps that mount the spine rod to the pedicle screws. In this scenario, it is also advantageous to have a device that will cut the rod on either side of the pedicle screw. Then the sections of the rod between screws can be easily lifted out. The remaining small sections of rod still attached to the pedicle screws can then be "helicoptered" out.

BRIEF SUMMARY OF THE INVENTION

In accordance with an exemplary embodiment of the subject disclosure, a cutter for cutting an implant is provided. The cutter includes a gearbox; a primary milling bit, a secondary milling bit and a lead screw operatively coupled to the gearbox; an input coupling coupled to the primary milling bit; and an implant coupler coupled to the lead screw, wherein the gearbox is operable to translate with respect to the lead screw and to drive the secondary milling bit in response to a driving force applied to the input coupling.

In accordance with another aspect of the subject disclosure, the gearbox includes a translation drive assembly operable to translate the gearbox with respect to the lead screw in response to the driving force applied to the input coupling, and a milling drive assembly operable to drive the secondary milling bit in response to the driving force applied to the input coupling.

In accordance with still another aspect of the subject disclosure, the translation drive assembly includes a first worm screw circumscribing and coupled to the primary milling bit; a first worm gear operatively coupled to the first worm screw; a second worm screw coupled rigidly to the first worm gear; a second worm gear operatively coupled to the second worm screw, the second worm gear circumscribing the lead screw and having a socket; and a nut in the socket of the second worm gear and threadedly engaging the lead screw.

In accordance with yet another aspect of the subject disclosure, the milling drive assembly includes a first spur gear circumscribing and coupled rigidly to the primary milling bit; a second spur gear operatively coupled to the first spur gear; and a third spur gear operatively coupled to the second spur gear and coupled to the secondary milling bit.

In accordance with other aspects of the subject disclosure, the first, second and third spur gears each include a same number of teeth. The input coupling includes a Hudson connector. The cutter further includes first and second chip collectors coupled to the gearbox and respectively circumscribing the primary and secondary milling bits. Each of the first and second chip collectors includes a cutout for receiving the implant and a chip collection cavity for maintaining chips and fragments milled from the implant. Each of the first and second chip collectors includes a longitudinal guide rail to slidably engage with a respective groove on the implant coupler.

In accordance with other aspects of the subject disclosure, the implant coupler includes a threaded receptacle coupled to a distal end of the lead screw and a helicopter socket to releasably couple to the implant. The implant coupler includes a recess for receiving a tulip of a screw. Each of the primary and secondary milling bits includes a distal cutting end with spiral flutes for cutting the implant and a proximal driving end operatively coupled to the gearbox. Each of the distal cutting ends includes rounded edges. Each of the primary and secondary milling bits comprise tungsten carbide. The primary milling bit, the secondary milling bit and the lead screw are spaced apart along a substantially linear path, and a longitudinal axis of the primary milling bit and a longitudinal axis of the secondary milling bit are substantially parallel to a longitudinal axis of the lead screw. The implant coupler is structured to couple to a spine rod. The input coupling is operable to receive a rotational driving force.

In accordance with other aspects of the subject disclosure, the implant cutter further comprises a clamping mechanism for applying a clamping force to an implant during cutting of the implant. According to an aspect, the clamping mechanism includes an axially extending shaft engaging the implant coupler, the shaft having a proximal end and an implant engageable tip at a distal end thereof operable to clampingly engage the implant. According to another aspect, the clamping mechanism includes a set screw extending through the implant coupler. According to another aspect, the clamping mechanism includes internal threads operable to threadedly engage the implant coupler, and a distal edge for clampingly engaging the implant.

In accordance with another exemplary embodiment of the subject disclosure, a cutter for cutting a spine rod affixed to a spine is provided. The cutter includes a gearbox having a distal end, a translation drive assembly and a milling drive assembly; a primary milling bit having a proximal drive end operatively coupled to the translation and milling drive assemblies and a distal cutting end; a secondary milling bit having a proximal drive end operatively coupled to the milling drive assembly and a distal cutting end for cutting the spine rod; a lead screw operatively coupled to the translation drive assembly and having proximal and distal ends; an input coupling coupled to the proximal drive end of the primary milling bit; a knob coupled to the proximal end of the lead screw; first and second chip collectors coupled to the distal end of the gearbox and respectively circumscribing the primary and secondary milling bits, each chip collector including a cutout for receiving the spine rod, a chip collection cavity for maintaining chips and fragments cut from the spine rod, and an outer surface provided with a longitudinally disposed guide rail; and an implant coupler having a proximal receptacle coupled to the distal end of the lead screw, first and second grooves sized to respectively and slidably engage with the guide rails of the first and second chip collectors, and a distal end having a socket structured to releasably couple to the spine rod.

In accordance with another aspect of the subject disclosure, the socket includes at least one receipt channel and at least one locking channel. In accordance with still another aspect of the subject disclosure, the input coupling is structured to releasably couple to a drill.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION OF THE INVENTION

Figure 1:
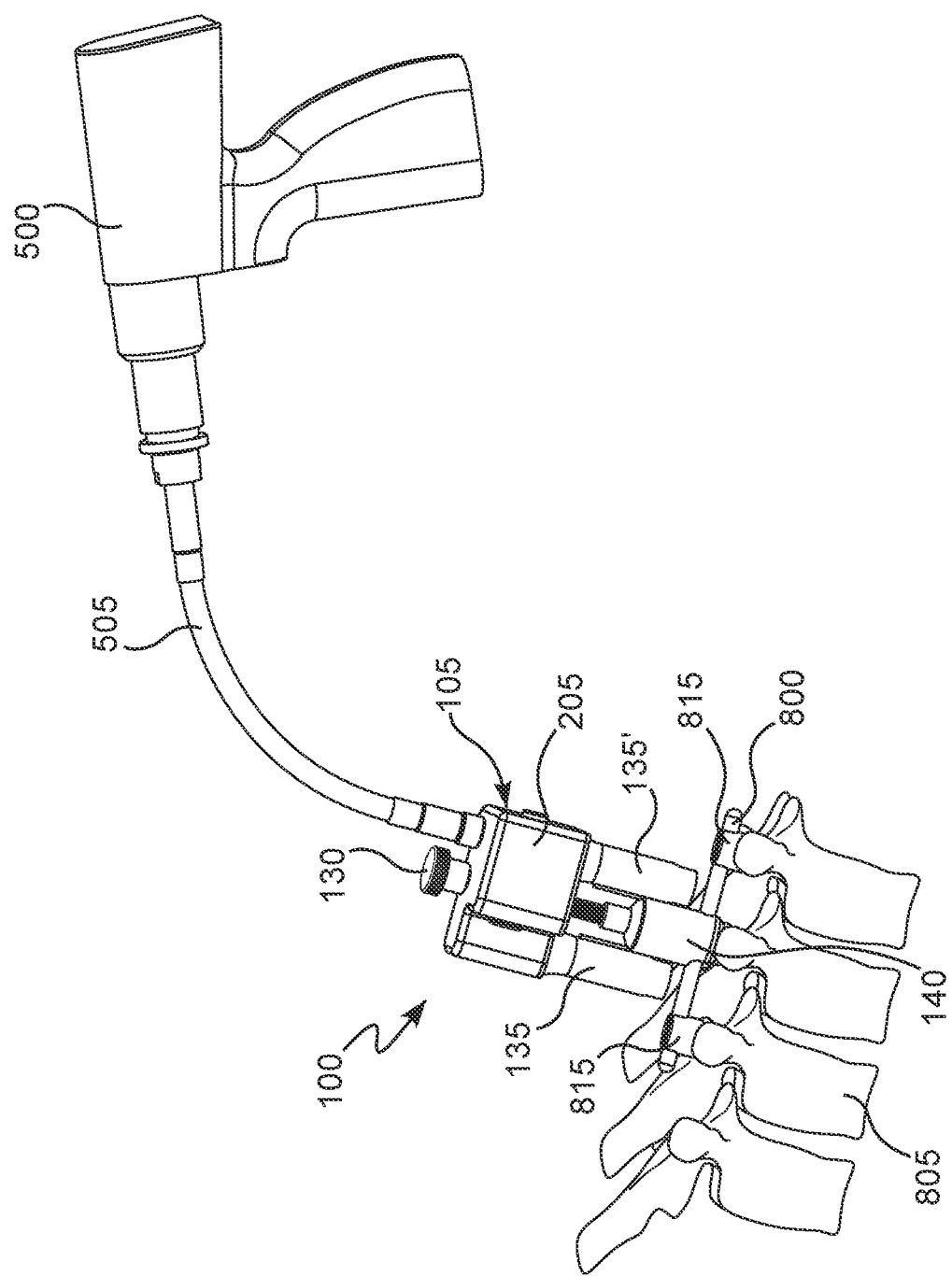
FIG. 1 is a perspective view of a cutter for cutting an implant in accordance with an exemplary embodiment of the subject disclosure coupled to a drill and positioned to cut a spine rod.
Figure 2:
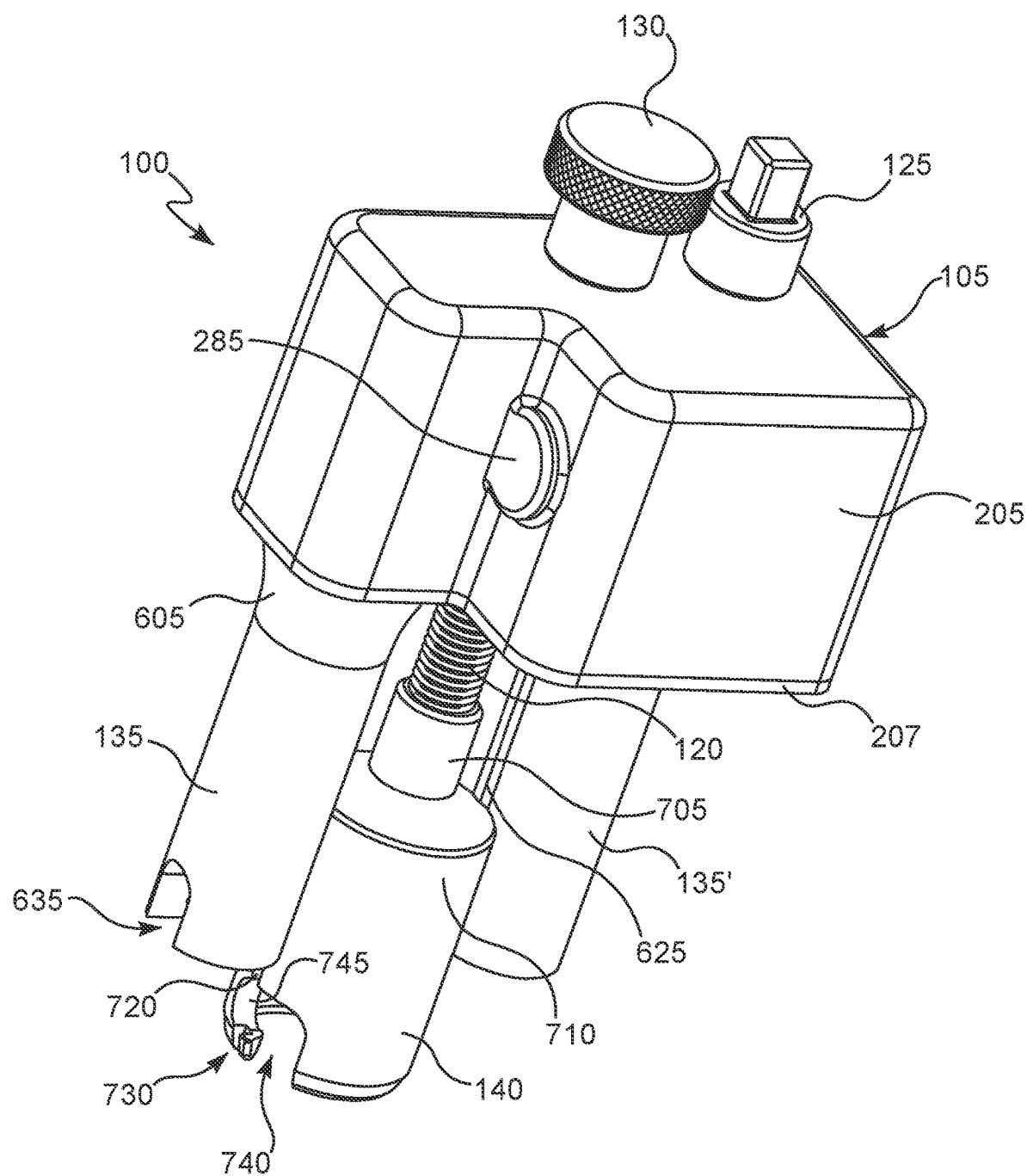
FIG. 2 is a perspective view of the cutter of FIG. 1.

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more exemplary embodiments. One skilled in the relevant art will recognize, in light of the description herein, that the subject disclosure can be practiced without one or more of the specific features or advantages of a particular exemplary embodiment. In other instances, additional features and advantages may be recognized in certain exemplary embodiments that may not be present in all exemplary embodiments of the present disclosure.

Referring now to the Figures, there is shown a cutter 100 in accordance with an exemplary embodiment of the subject disclosure. The cutter 100 may be used to cut/mill spine rods, including, for example, a spine rod 800 affixed to a spine 805 of a patient using spine rod screws 810 having proximally attached tulips 815 (see FIGS. 1 and 10A through 10D). The cutter 100 may be employed, for example, to cut implanted spine rods of varying lengths and diameters (e.g., 2, 4, 6, 8, 10 mm, etc.), as well as those affixed to a spine using structures other than screws 810 and those constructed from various materials, such as, for example, stainless steel, titanium, or cobalt chrome. Although the cutter 100 is described herein and shown in the Figures as operable to cut spine rods (such as spine rod 800), it should be appreciated that the cutter 100 and other embodiments contemplated by the subject disclosure may be used to cut/mill other types of implants, and that various embodiments of the subject disclosure are not intended to be limited for use with any particular size, type or category of implant(s).

As best shown in FIGS. 2 through 5 and 10A through 10D, the cutter 100 includes a gearbox 105, primary and secondary milling bits 110, 110', and a shaft e.g., a threaded lead screw 120 operatively coupled to and extending through the gearbox 105, an input coupling 125 (which e.g., may include a Hudson connector or similar connector for coupling to a driving source) coupled rigidly to the proximal end of the primary milling bit 110, a knob 130 coupled to the proximal end of the lead screw 120, chip collectors 135, 135' coupled to the distal end of the gearbox 105 and respectively circumscribing the primary and secondary milling bits 110, 110', and an implant coupler 140 coupled to the distal end of the lead screw 120 and guided for longitudinal translation by the chip collectors 135, 135', e.g., via guide rails 625, 625'. In the illustrated exemplary embodiment, the primary milling bit, the secondary milling bit and the lead screw are spaced apart along a substantially linear path, and a longitudinal axis of the primary milling bit and a longitudinal axis of the secondary milling bit are substantially parallel to a longitudinal axis of the lead screw.

Figures 3, 4:
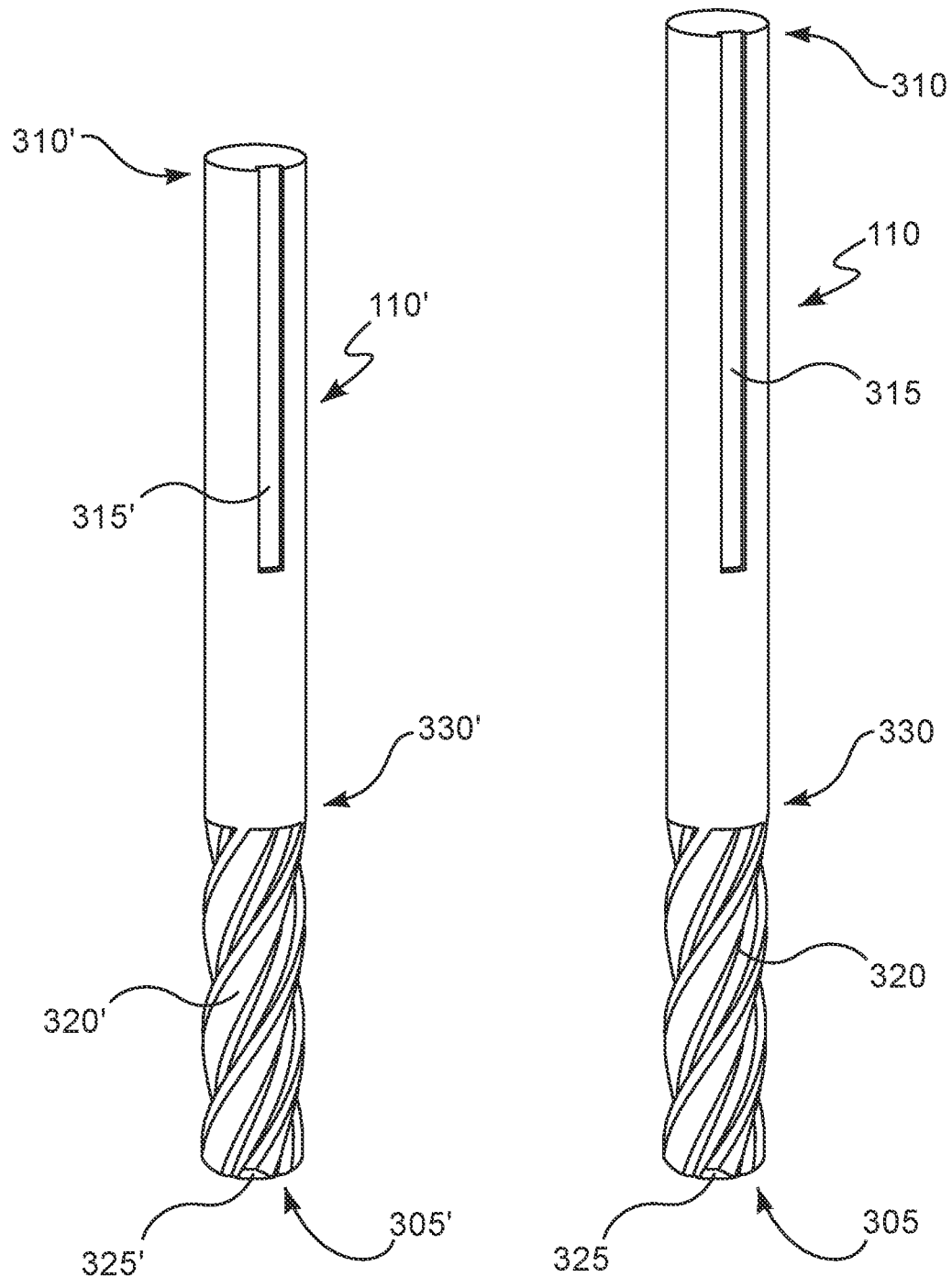
FIGS. 3 and 4 are perspective views of primary and secondary milling bits of the cutter of FIG. 1.

As best shown in FIGS. 3 and 4, the primary and secondary milling bits 110, 110' respectively include distal cutting ends 305, 305' for cutting implants e.g., the spine rod 800, and proximal drive ends 310, 310' with respective drive grooves 315, 315' for operatively coupling to the gearbox 105. The cutting ends 305, 305' include notched or rounded edges 325, 325' to reduce chipping and spiral flutes 320, 320' for transporting chips and other fragments cut/milled from the spine rod 800 proximally toward center regions 330, 330' of the bits 110, 110'. In one exemplary embodiment, at least the cutting ends 305, 305' of the primary and secondary milling bits 110, 110' are made from tungsten carbide, though it should be appreciated that other portions of the milling bits 110, 110' may also be made of tungsten carbide, or that any or all portions thereof may be constructed using alternative materials. It should also be appreciated that the cutting ends 305, 305' may be center or edge cutting and/or or have rounded edges 325, 325', and that various exemplary embodiments of the subject disclosure are not intended to be limited to any particular type of cutting end or manner of cutting the spine rod 800 or other implant.

With reference to FIGS. 2 and 5 through 7, the gearbox 105 includes a housing 205 with a distal plate 207 enclosing translation and milling drive assemblies 210, 215 operable respectively to translate the gearbox 105 distally with respect to the lead screw 120 or along a longitudinal extent of the lead screw and to drive the secondary milling bit 110' in response to a rotational driving force applied to the input coupling 125, as well as various washers 270 and bushings 275*a*, 275*b*, 275*c*, 275*d*, 275*e* and 275*f* to protect the various components of the drive assemblies 210, 215 from wear and to properly position, align and space the components within the housing 205. In the exemplary embodiment depicted in the Figures, the driving force is supplied e.g., by a drill 500 with a flexible drive shaft 505, though it should be appreciated that the rotational driving force may be applied to the input coupling 125 in other ways, such as, for example, via a rigid drive shaft, and that various exemplary embodiments of the subject disclosure are not intended to be limited to any particular manner of applying a driving force to the input coupling 125.

Figure 5:
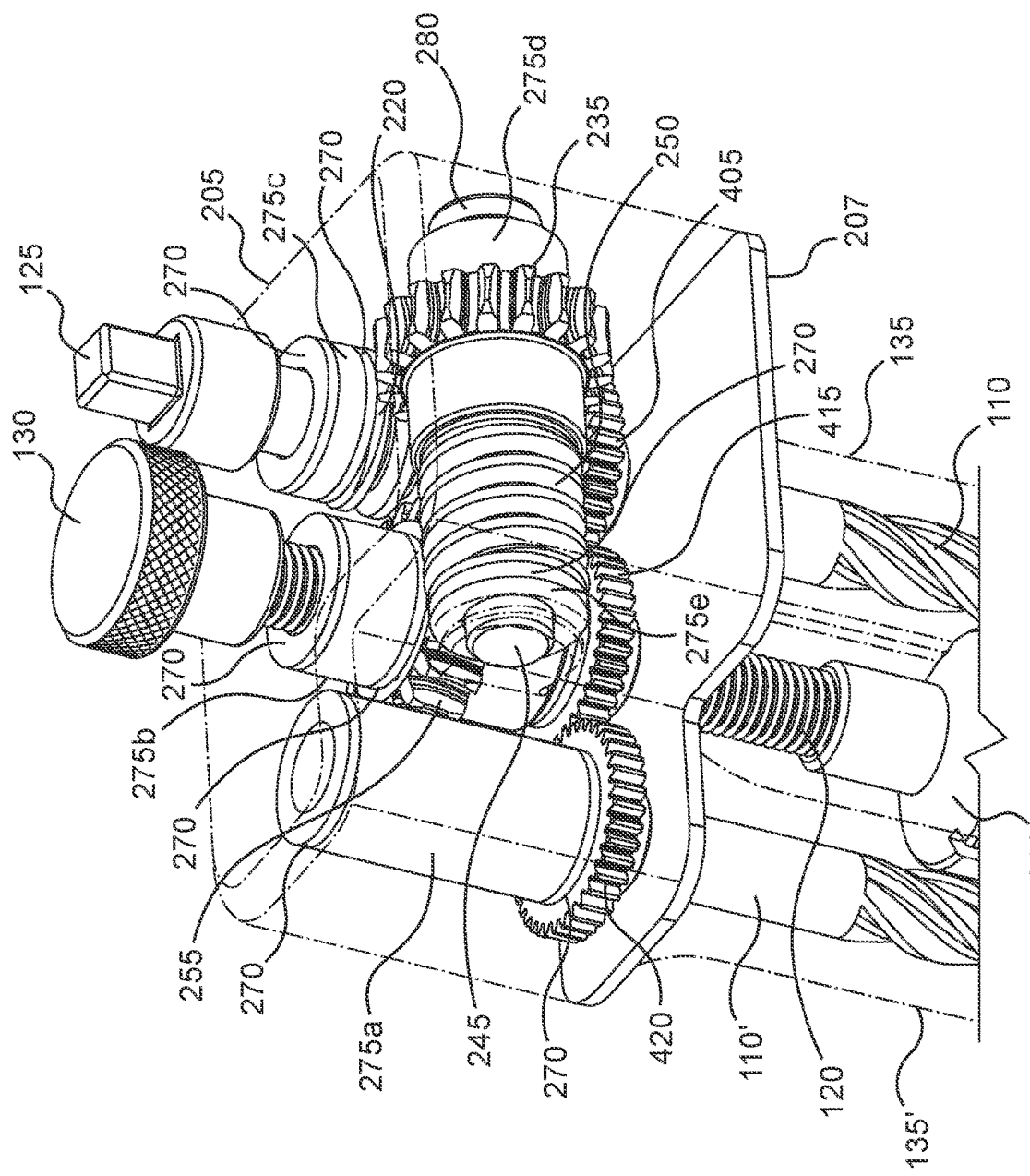
FIG. 5 is a partial perspective view of the cutter of FIG. 1 with the housing shown in phantom for purposes of illustration.
Figure 6:
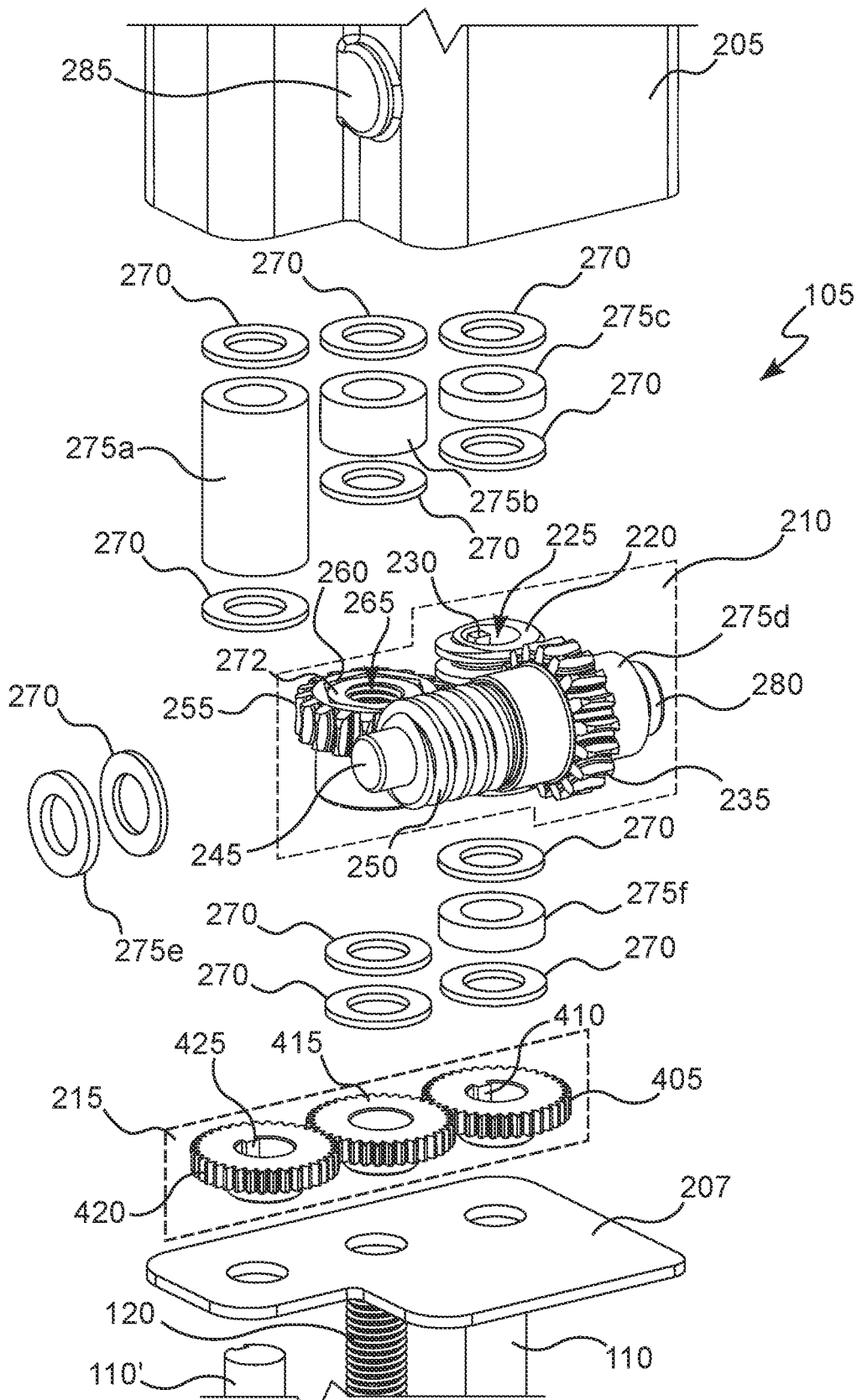
FIG. 6 is a partially exploded perspective view of the cutter of FIG. 1.
Figure 7:
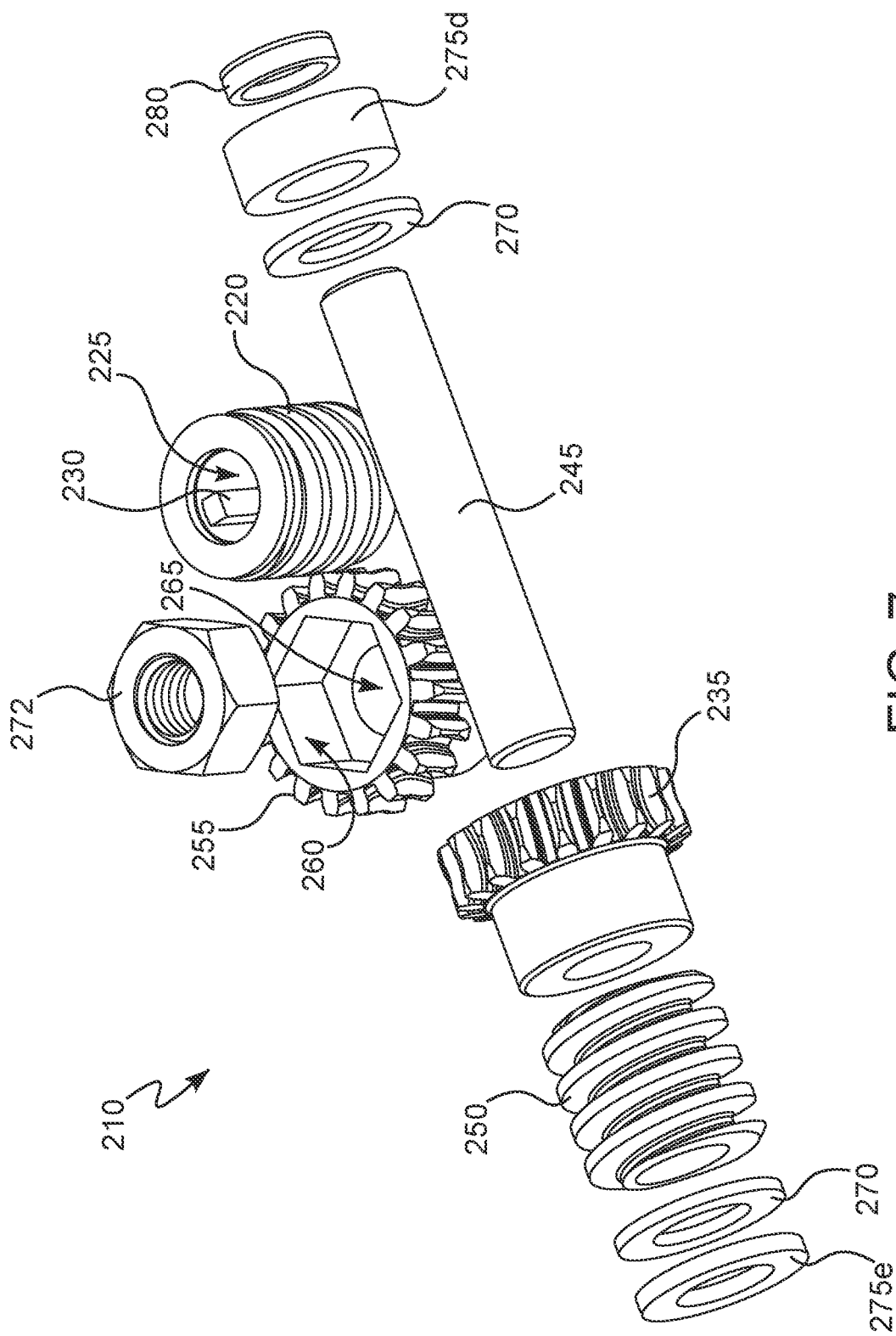
FIG. 7 is an exploded perspective view of a translation drive assembly of the cutter of FIG. 1.
Figure 8A:
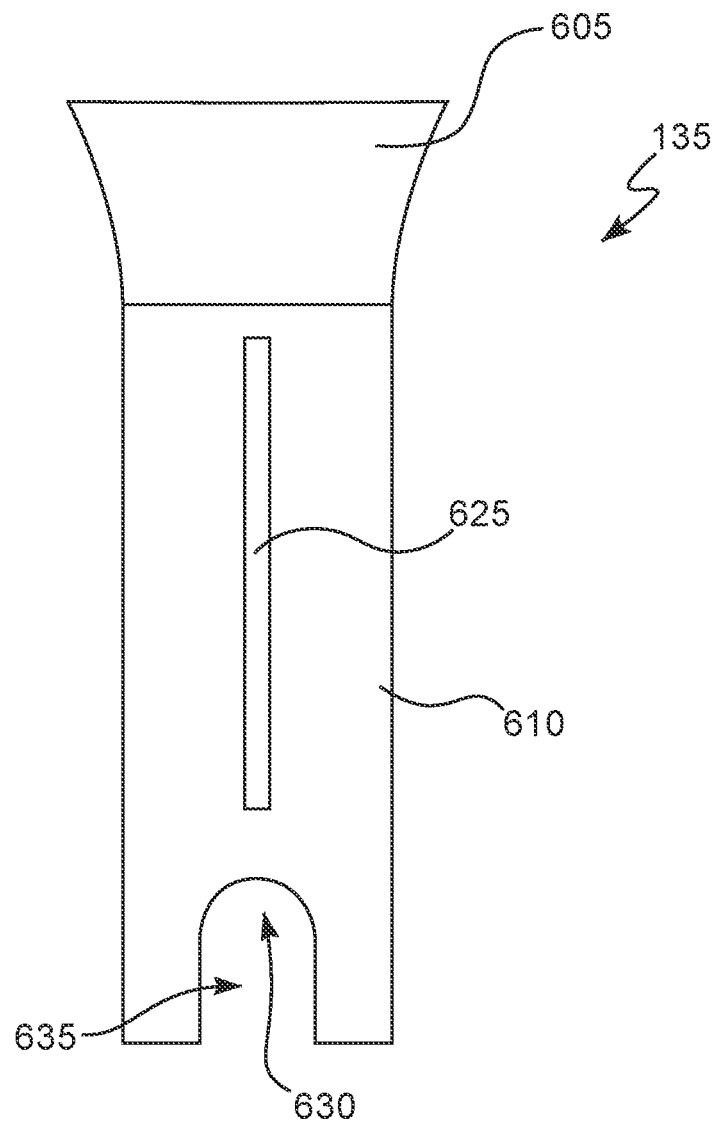
FIG. 8A is a side view of a chip collector of the cutter of FIG. 1.
Figure 8B:
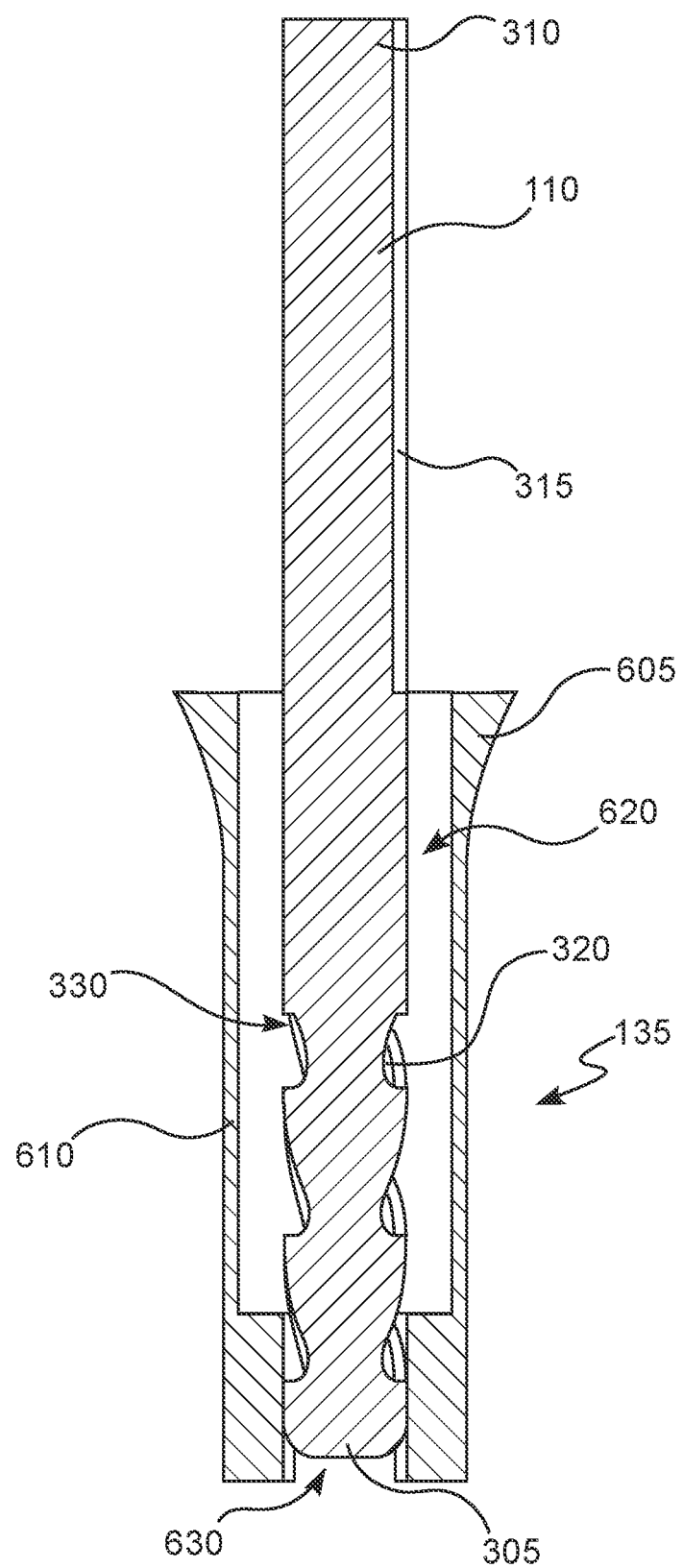
FIG. 8B is a longitudinal sectional view of the chip collector of FIG. 8A circumscribing a milling bit.
Figure 8C:
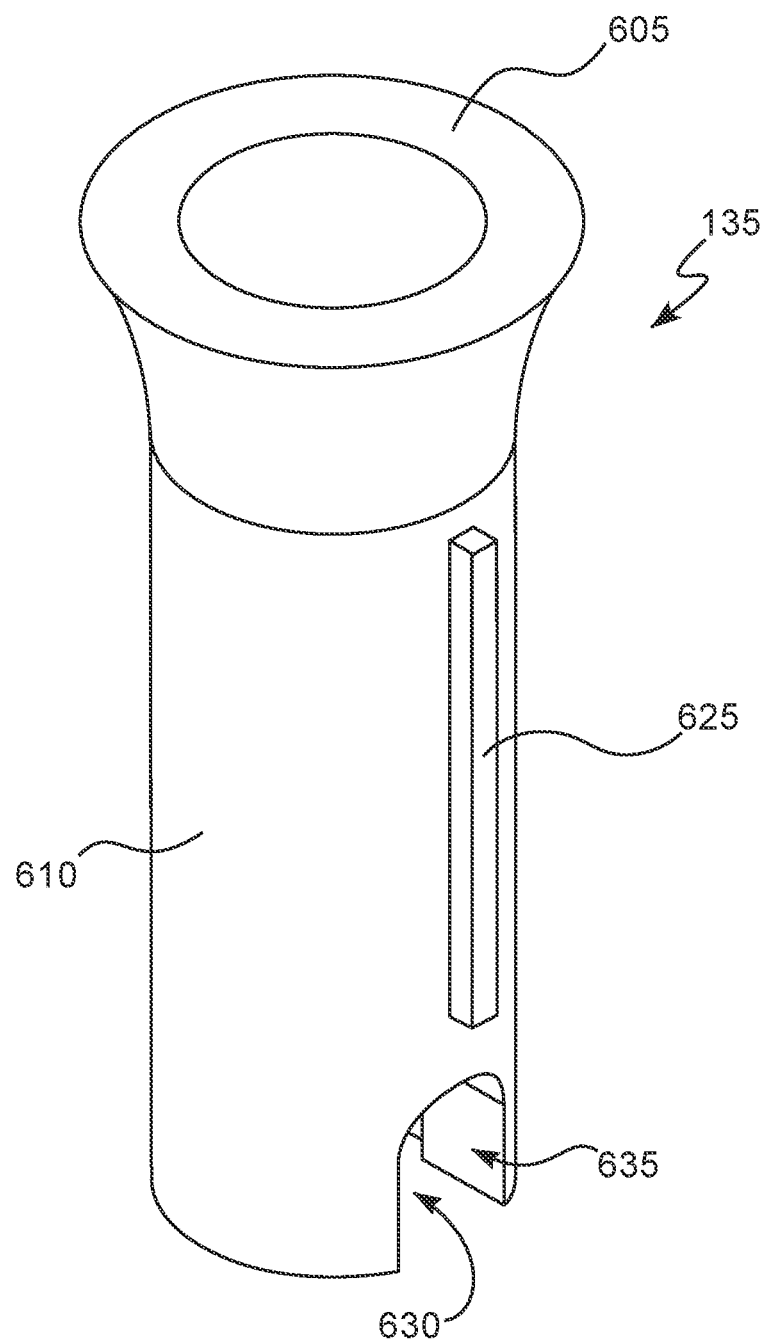
FIG. 8C is a perspective view of the chip collector of FIG. 8A.
Figure 9A:
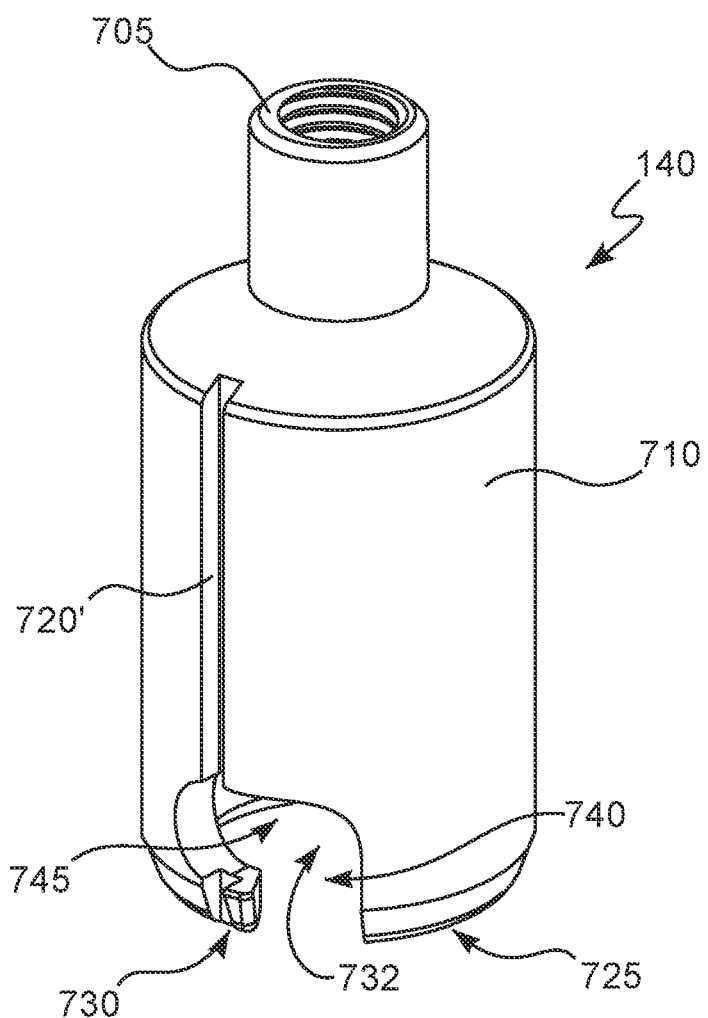
FIG. 9A is a perspective view of an implant coupler of the cutter of FIG. 1.
Figure 9B:
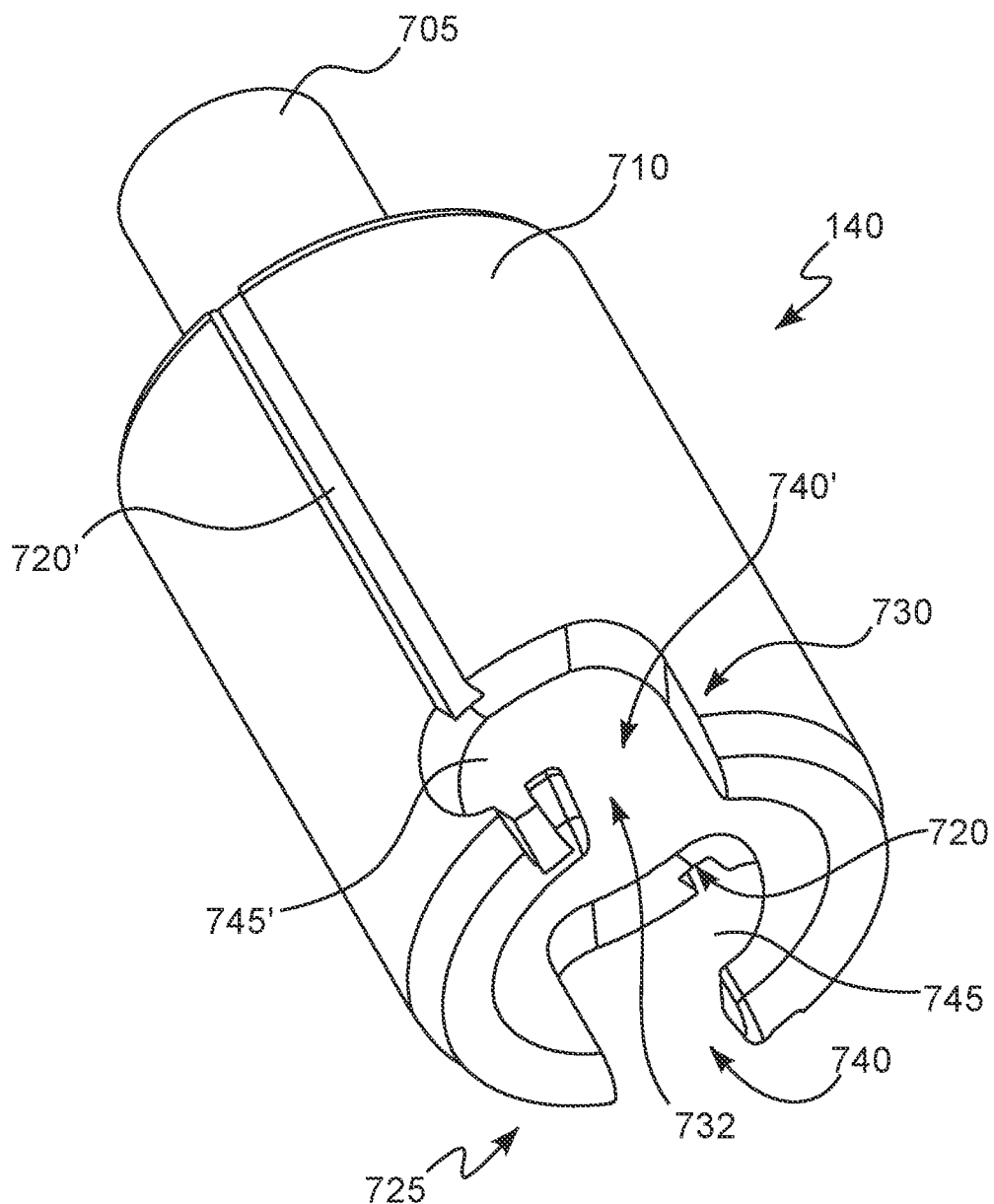
FIG. 9B is another perspective view of the implant coupler of FIG. 9A.

As best shown in FIGS. 5 through 7, the translation drive assembly 210 includes a first worm screw 220 having a longitudinal bore 225 receiving the proximal drive end 310 of the primary milling bit 110 and a longitudinally extending drive rib 230 engaging the drive groove 315 of the primary milling bit 110, a first worm gear 235 operatively coupled to the first worm screw 220, a shaft 245 extending longitudinally through the first worm gear 235 and bounded at one end by an end cap 280 and circlip (not shown) inside the housing 205 and on the other end by an alignment receptacle 285 (FIG. 10D) on the inside of the housing 205, a second worm screw 250 disposed rotatably on and circumscribing the shaft 245 and coupled rigidly to the first worm gear 235, a second worm gear 255 operatively coupled to the second worm screw 250 and having a hexagonal socket 260 and a longitudinal through bore 265 circumscribing the lead screw 120, and a hexagonal lead nut 272 positioned within the hexagonal socket 260 and threadedly engaged with the lead screw 120.

As best shown in FIGS. 5 and 6, the milling drive assembly 215 includes a first spur gear 405 circumscribing the primary milling bit 110 distally of the first worm screw 220 and having a longitudinally extending drive rib 410 engaging the drive groove 315 of the primary milling bit 110, a free-spinning second spur gear 415 operatively engaging the first spur gear 405 and rotatably circumscribing the lead screw 120 distally of the second worm gear 255, and a third spur gear 420 operatively engaging the second spur gear 415, circumscribing the secondary milling bit 110' and having a longitudinally extending drive rib 425 engaging the drive groove 315' of the secondary milling bit 110'.

Although the components of the translation and milling drive assemblies 210, 215 described herein and illustrated in the Figures operate together to translate the gearbox 105 distally with respect to the lead screw 120 and to drive the secondary milling bit 110', it should be appreciated that the translation and milling drive assemblies 210, 215 may include other arrangements of the same or different components to effectuate these functions, and that various embodiments of the subject disclosure are not intended to be limited to any specific components or arrangement of components for translating the gearbox 105 or driving the secondary milling bit 110'. It should also be appreciated that the translation and milling drive assemblies 210, 215 may include non-gear components, such as hydraulic and/or electrical components, and that various embodiments of the subject disclosure are not intended to be limited to any type or class of components.

As best shown in FIGS. 2, 8A through 8C, and 10A through 10D, the chip collectors 135, 135' circumscribe the primary and secondary milling bits 110, 110' and respectively include proximal funnel-shaped ends 605, 605' coupled to the distal plate 207 of the housing 205, generally cylindrical body portions 610 having internal chip collection cavities 620 in communication with the milling bits 110, 110' and outer surfaces provided with longitudinally extending guide rails 625, 625', longitudinal bores 630 extending from the distal bottoms of chip collection cavities 620 to the distal ends of the body portions 610, 610', and cutouts 635 shaped to receive the spine rod 800 and facing transversely to and intersecting the longitudinal bores 630 at the distal ends of the body portions 610, 610'. The internal diameters of bores 630 at the distal ends of the chip collectors are equal to or slightly larger than the external diameters of the primary and secondary milling bits 110, 110' to effectively retain or seal the chip collection cavities 620 and prevent chips and other fragments removed from the spine rod 800 from escaping the cavities 620. In the exemplary embodiment depicted in the Figures, the cutouts 635 are U-shaped to receive the spine rod 800, though it should be appreciated that the cutouts 635 may be shaped differently to receive other types of implants.

As best shown in FIGS. 2 and 9A through 10D, the implant coupler 140 includes a proximal threaded receptacle 705 coupled to the distal end of the lead screw 120 and a generally cylindrical coupling body 710 having an outer surface provided with longitudinally extending grooves 720, 720' respectively and slidably engaging with the guide rails 625, 625' of the chip collectors 135, 135' and a distal end 725 provided with a socket 730 e.g., a helicopter socket and a hollow receptacle 732 shaped e.g., to receive a tulip 815 of a spine rod screw 810 for properly orientating and aligning the cutter 100 during a cutting/milling operation. In alternative exemplary embodiments, the implant coupler may or may not include a hollow receptacle e.g., the implant coupler may be of smaller diameter or a cylinder having a socket for engaging a rod similar to socket 730. In this alternative embodiment, the coupler does not receive the tulip 815 and engages only with the spine rod 800.

The socket 730 is shaped to releasably receive the spine rod 800 and includes helicopter cutouts having respective and radially aligned or diametrically opposed receipt channels 740, 740' and locking channels 745, 745'. The locking channels 745, 745' are also configured to align planarly with the cutouts 635 of the chip collectors 135, 135' so that the primary and secondary milling bits 110, 110' can properly align with the spine rod 800 during operation of the cutter 100. It should be appreciated that the receipt channels 740, 740' and locking channels 745, 745' may be shaped differently to receive differently shaped rods and other implants. It should also be appreciated that the implant coupler 140 may include structures in addition to or in lieu of the socket 730 for releasably receiving the spine rod 800 or other implant.

Figure 10A:
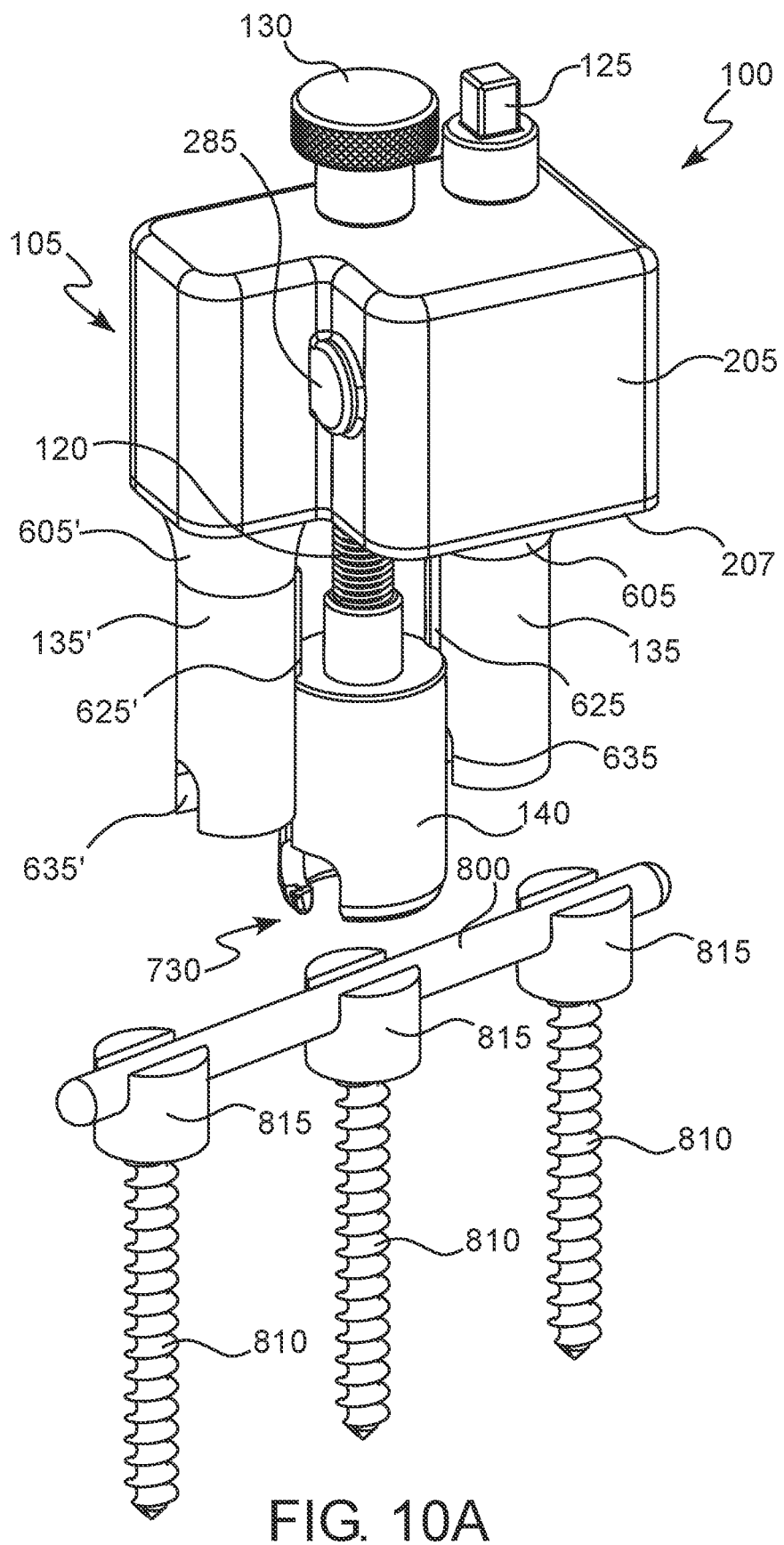
FIG. 10A is a perspective view of the cutter of FIG. 1 aligned above a spine rod.
Figure 10B:
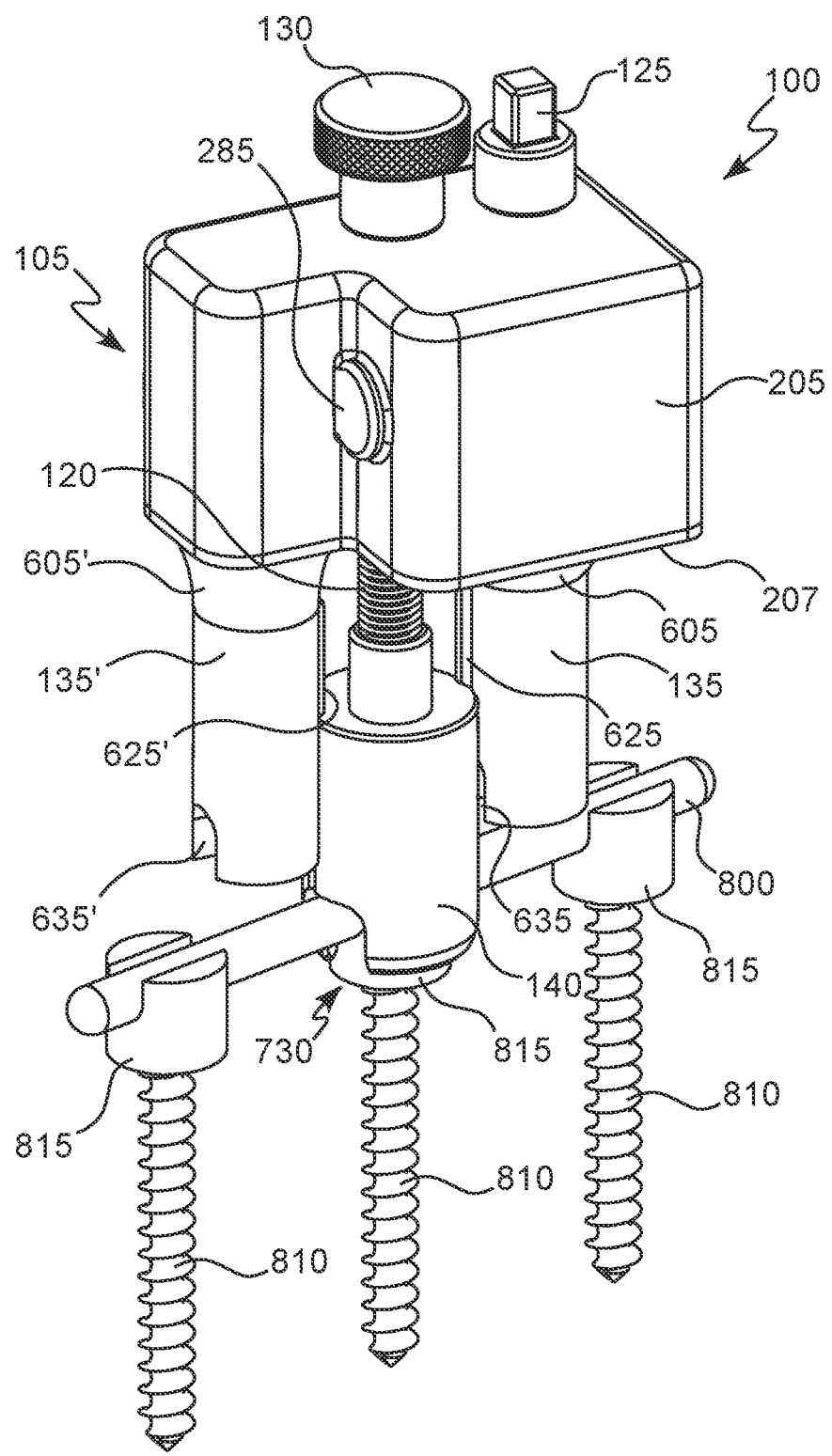
FIG. 10B is a perspective view of the cutter of FIG. 1 engaged with a spine rod.
Figure 10C:
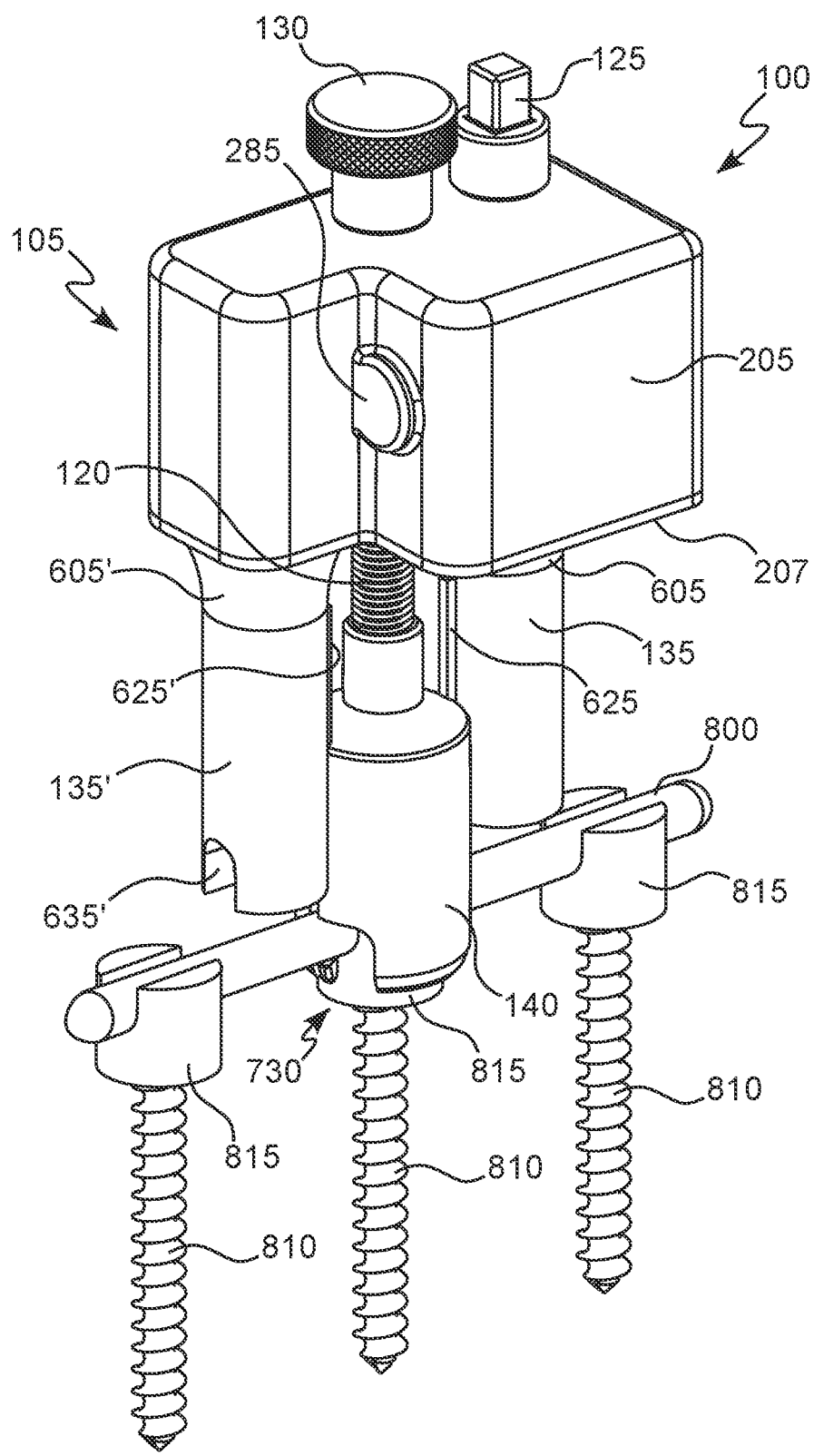
FIG. 10C is a perspective view of the cutter of FIG. 1 engaged with and releasably coupled to a spine rod.
Figure 10D:
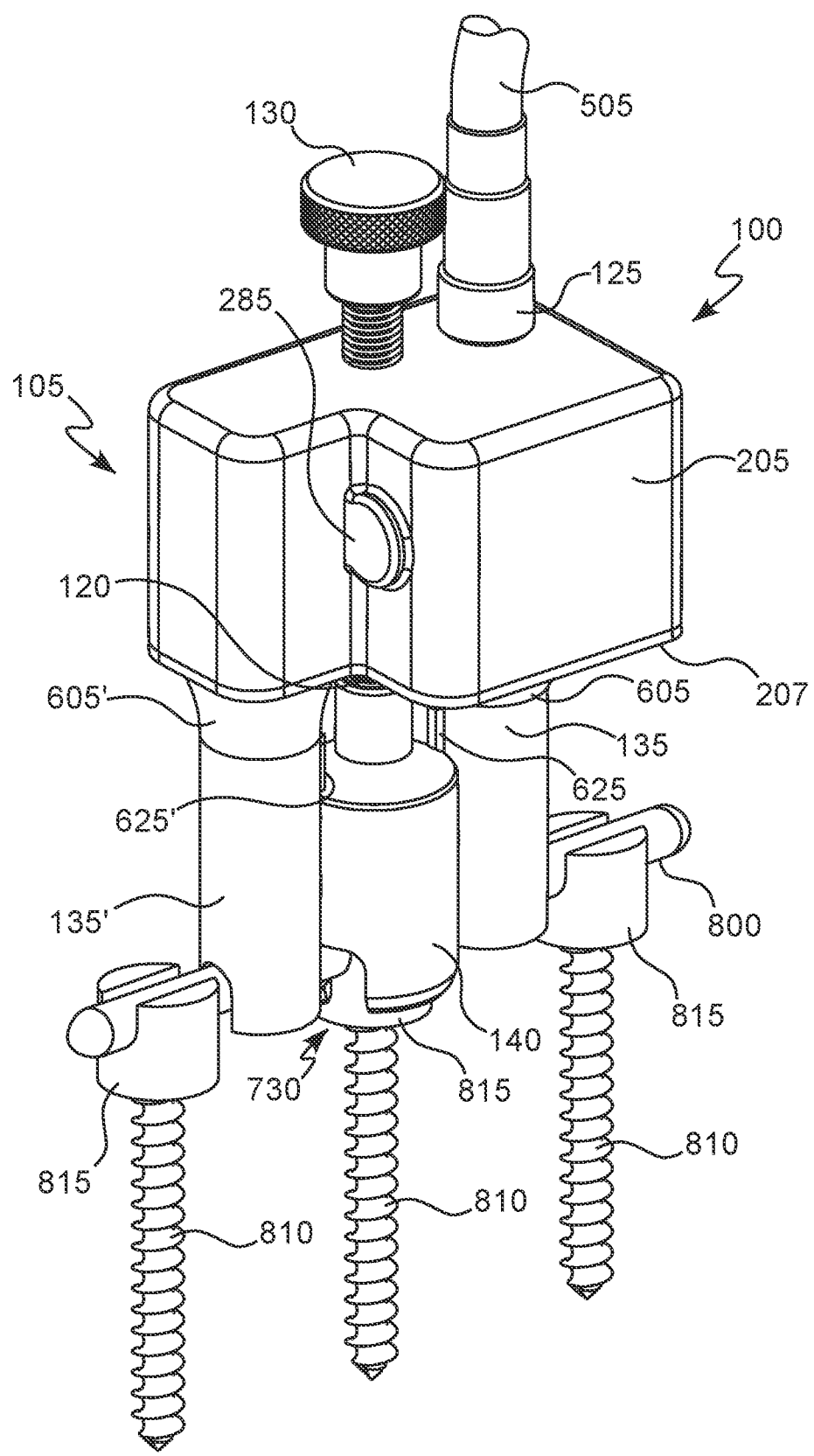
FIG. 10D is a perspective view of the cutter of FIG. 1 cutting a spine rod.

To operate the cutter 100 to cut/mill the spine rod 800, a user first aligns the cutter 100 (see FIG. 10A) and engages the hollow receptacle 732 of the implant coupler with a tulip 815 of a spine rod screw 810, while at the same time aligning the receipt channels 740, 740' of the implant coupler 140 with the spine rod 800 (see FIG. 10B). Once the spine rod 800 is received completely within the receipt channels 740, 740' of the implant coupler 140, the user rotates the cutter 100 counterclockwise (when viewed distally from the proximal side of the cutter 100) to position the spine rod 800 fully within the locking channels (see FIG. 10C), thereby locking the spine rod 800 rigidly in position with respect to the cutter 100 and aligning the primary and secondary milling bits 110, 110' with the spine rod 800. The user then applies a clockwise driving force to the input coupling 125. Clockwise rotation of the input coupling 125 drives the primary milling bit 110, which in turn causes the drive groove 315 of the primary milling bit 110 to engage the drive rib 410 of the first spur gear 405 and rotate the gear 405 clockwise with the primary milling bit 110. Rotation of the first spur gear 405 causes the free-spinning second spur gear 415 to rotate counterclockwise about the lead screw 120 which, in turn, causes the third spur gear 420 to rotate clockwise. As the third spur gear 420 rotates, the drive rib 425 of the third spur gear 420 engages the drive groove 315' of the secondary milling bit 110' causing the bit 110' to also rotate clockwise with the third spur gear 420. Since the first, second and third spur gears 405, 415, 420 are similarly sized and include the same number of teeth, the third spur gear 420 rotates at the same speed and in the same clockwise direction as first spur gear 405 to ensure that the primary and secondary milling bits 110, 110' rotate clockwise at the same speed. It should be appreciated, however, that the spur gears 405, 415, 420 may be sized differently and/or include different numbers of teeth, and that the secondary milling bit 110' may rotate at a different speed or in a different rotational direction compared to the primary milling bit 110.

Rotation of the primary milling bit 110 also causes the drive groove 315 of the primary milling bit 110 to engage the drive rib 230 of the first worm screw 220 causing it to rotate clockwise with the primary milling bit 110. Rotation of the first worm screw 220 causes rotation of the first worm gear 235 and second worm screw 250 about the shaft 245 which, in turn, causes clockwise rotation of the second worm gear 255 and hexagonal lead nut 272 about the lead screw 120. Since the lead nut 272 threadedly engages with the lead screw 120 and because engagement of the implant coupler 140 with the spine rod 800 prevents longitudinal displacement of the lead screw 120, the clockwise rotation of the hexagonal lead nut 272 causes the lead screw 120 to produce a distal force on the lead nut 272, thereby causing the gearbox 105 (with coupled milling bits 110, 110' and chip collectors 135, 135') to translate distally along the lead screw 120 guided by engagement of the guide rails 625, 625' of the chip collectors 135, 135' with the grooves 720, 720' of the implant coupler 140. In another embodiment, the device may use a compound gear set instead of worm drive gears.

The gearbox 105 translates distally until the distal cutting ends 305, 305' of the primary and secondary milling bits 110, 110' contact the spine rod 800, at which point cutting/milling of the spine rod 800 begins. The cutouts 635 of the chip collectors 135, 135' engage with the spine rod 800 and help guide the milling bits 110, 110' as they advance therethrough. Chips and other fragments removed from the spine rod 800 are transported proximally by the spiral flutes 320, 320' of the primary and secondary milling bits 110, 110' into the chip collection cavities 620 of the chip collectors 135, 135', where they are deposited and maintained during the cutting/milling operation. The primary and secondary milling bits 110, 110' continue to translate distally until they cut through the spine rod 800, at which point the cutting/milling operation ends (FIG. 10D) and the cutter 100 is removed from the patient.

Over cutting is prevented by the proximal top surfaces of cutouts 635 which engage with the spine rod 800 to prevent the distal center-cutting ends 305, 305' of the primary and secondary milling bits 110, 110' from translating too far distally into the patient. In other words, owing to their abutment with the spine rod, the proximal top surfaces of cutouts of the chip collectors prevent further distal penetration of the cutting ends of the primary and secondary milling bits once the spine rod is cut thereby. For example, the largest diameter of spine rods is currently 6 mm. Therefore, there will be a hard stop on the travel of the cutters at a distance slightly greater than 6 mm. The cylindrical guides concentric to the cutters have a cutout that accepts the spine rod. The furthest travel of the cutters is limited to not extend past these guides.

After completion of the cutting/milling operation, the chip collectors 135, 135' are removed from the cutter 100 so that the chips and other fragments cut/milled from the spine rod 800, as well as any chips and fragments remaining in the spiral flutes 320, 320' of the primary and secondary milling bits 110, 110', may be accessed and discarded. In at least some exemplary embodiments, removal of the chip collectors 135, 135' may be facilitated by first detaching the implant coupler 140 from the cutter 100. This may be effectuated by first rotating the knob 130 counterclockwise to retract the distal end of the lead screw 120 from the threaded receptacle 705 of the implant coupler 140 and then sliding the coupler 140 distally to disengage the guide rails 625, 625' of the chip collectors 135, 135' from the grooves 720, 720' of the implant coupler 140. The cutter 100 may then be reset to perform a new cutting/milling operation by first reattaching the chip collectors 135, 135' and the implant coupler 140 and then translating the gearbox 105 proximally into its initial position by applying a counterclockwise rotational force to the input coupling 125 manually or by using the drill 500 or other mechanism.

FIGS. 11, 12, 13A and 13B disclose further exemplary embodiments of the subject disclosure, which include a clamping mechanism for applying clamping force to an implant during cutting of the implant. The various clamping mechanisms of these embodiments hold the implant firmly and steady in place to prevent chattering of the implant, i.e., resist vibrations of the implant, caused by milling. For brevity, only those elements of the implant cutters shown in FIGS. 11, 12, 13A and 13B that materially depart in structure and/or function from their counterparts shown in FIGS. 1-10D, or are otherwise necessary for a proper understanding of the subject disclosure, will be described in detail.

Figure 11:
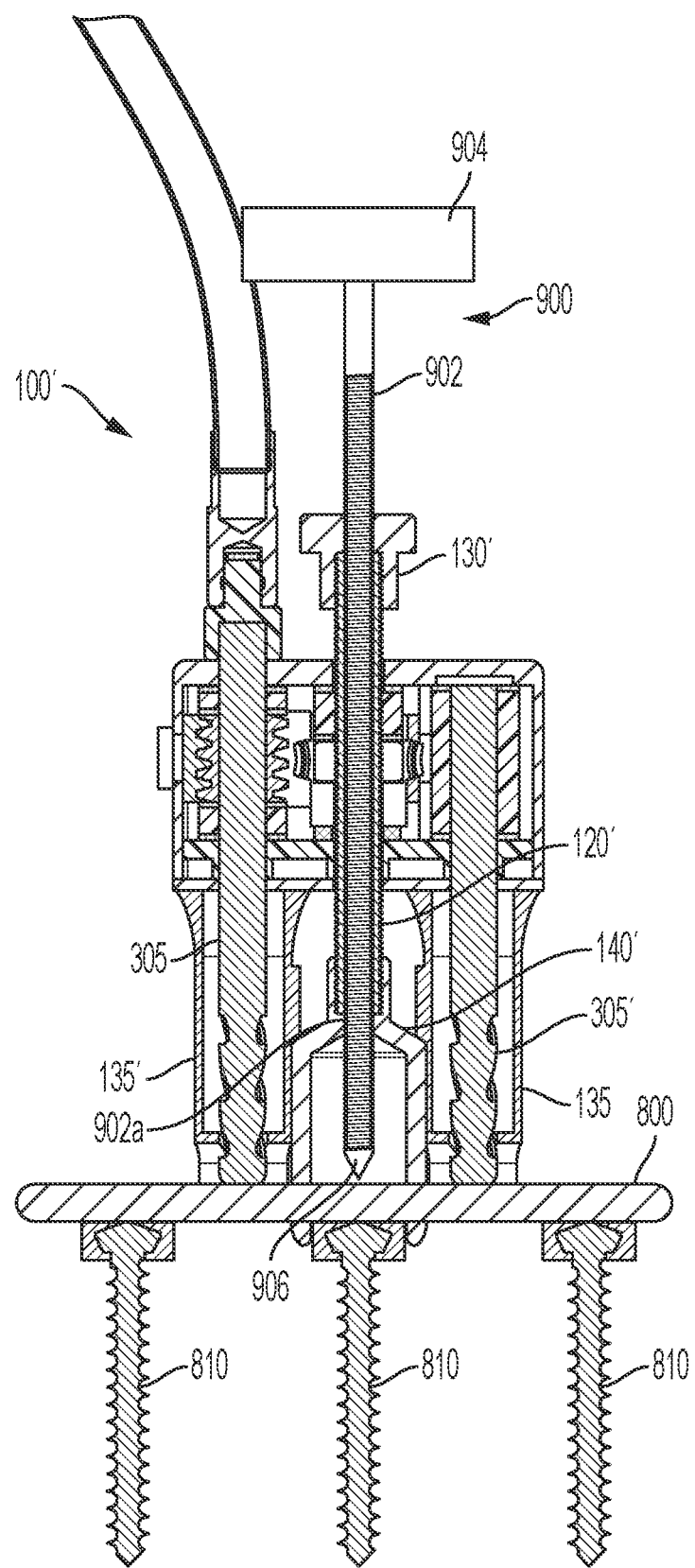
FIG. 11 is an elevational, cross-sectional view of another exemplary embodiment of a cutter for cutting an implant in accordance with the subject disclosure.

Referring to FIG. 11, there is shown an exemplary embodiment of a clamping mechanism 900 operatively connected to the implant coupler 140' for applying a clamping force to an implant 800 during cutting of the implant. The clamping mechanism 900 comprises an axially extending elongated shaft 902 have threads threadedly engaging the implant coupler e.g., about its proximal end 902a. The threaded shaft includes a handle 904 at a proximal end thereof and an implant engageable tip 906 at a distal end thereof operable to clampingly engage the implant, e.g., spine rod 800. While the elongated threaded shaft 902 threadedly engages at least the implant coupler 140', it is understood that one or both of knob 130' and threaded lead screw 120' may be correspondingly internally threaded to engage with the external threading of the shaft 902. That is the lead screw 120' and/or knob 130' can include a longitudinal through hole having internal threads. However, to minimize resistance to turning of the threaded shaft by the handle 904, the knob 130' and the threaded lead screw 120' are provided with smooth-walled internal bores of slightly larger diameter than the diameter of the threaded shaft.

In operation, and prior to milling of the implant 800, the implant coupler is engaged with the implant as described above. Thereafter, the handle 904 is turned in a direction to advance the threaded shaft and tip 906 towards the implant 800 until the tip comes into firm direct engagement with the implant. With the implant firmly engaged, the above-described milling operation is performed with minimal or no vibration of the implant occurring during milling, whereby the implant is easily and precisely cut by the implant cutter 100'.

Figure 12:
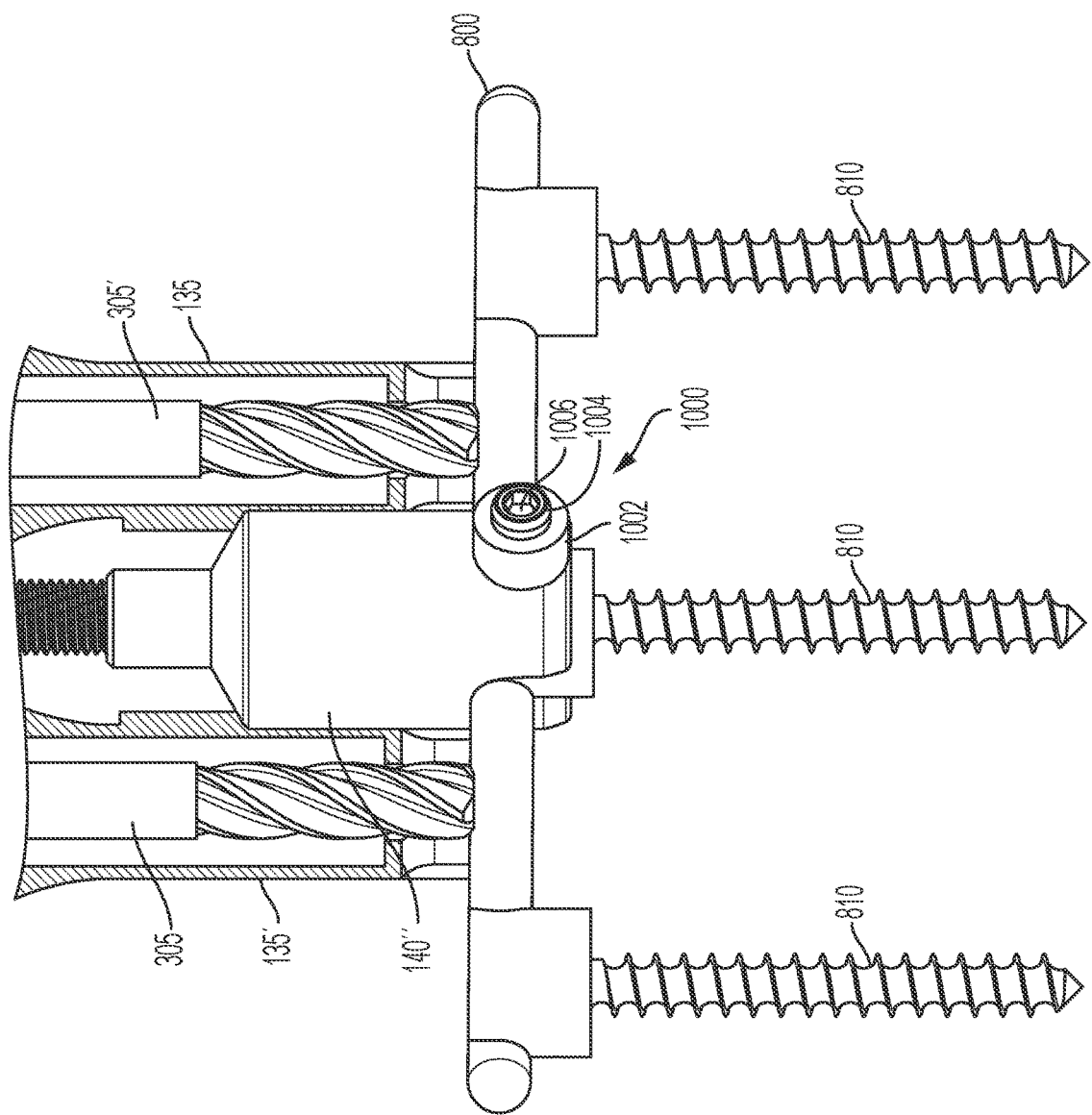
FIG. 12 is a perspective view of a lower portion of another exemplary embodiment of a cutter for cutting an implant in accordance with the subject disclosure.

Referring to FIG. 12, there is shown another exemplary embodiment of a clamping mechanism 1000 operatively connected to the implant coupler 140" for applying a clamping force to an implant 800 during cutting of the implant. The clamping mechanism 1000 comprises a set screw receiver 1002 radially or laterally projecting from the implant coupler 140" and a laterally extending set screw 1004 threadedly engaging the implant coupler at the set screw receiver and operable to clampingly engage the implant. The set screw has a socket 1006 or other tool engageable structure that permits the set screw to be advanced into the implant coupler until it firmly engages the implant. Milling of the implant can then be performed with minimal or no vibration of the implant occurring during milling.

Figure 13A:
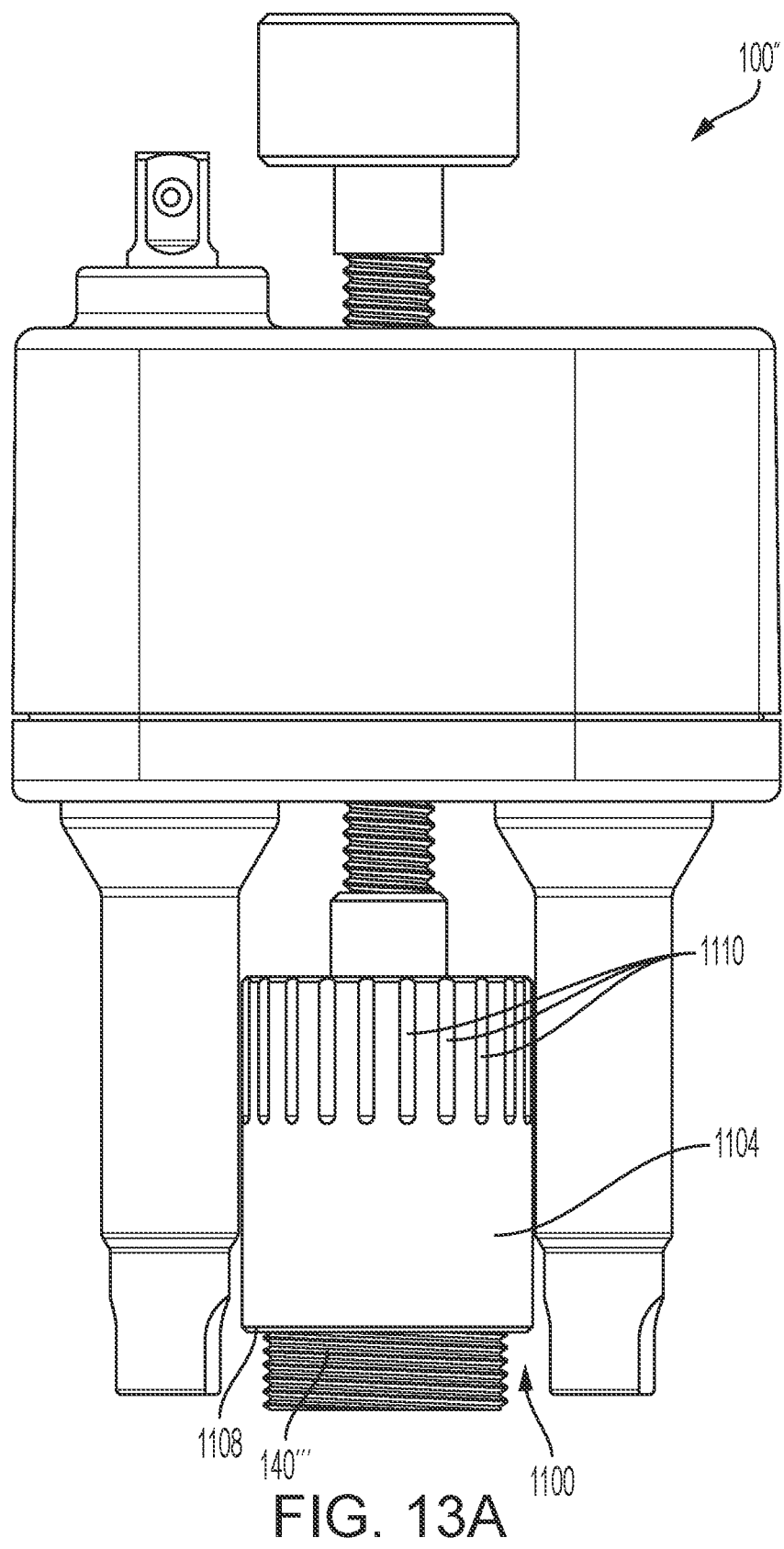
FIG. 13A is an elevational view of another exemplary embodiment of a cutter for cutting an implant in accordance with the subject disclosure.
Figure 13B:
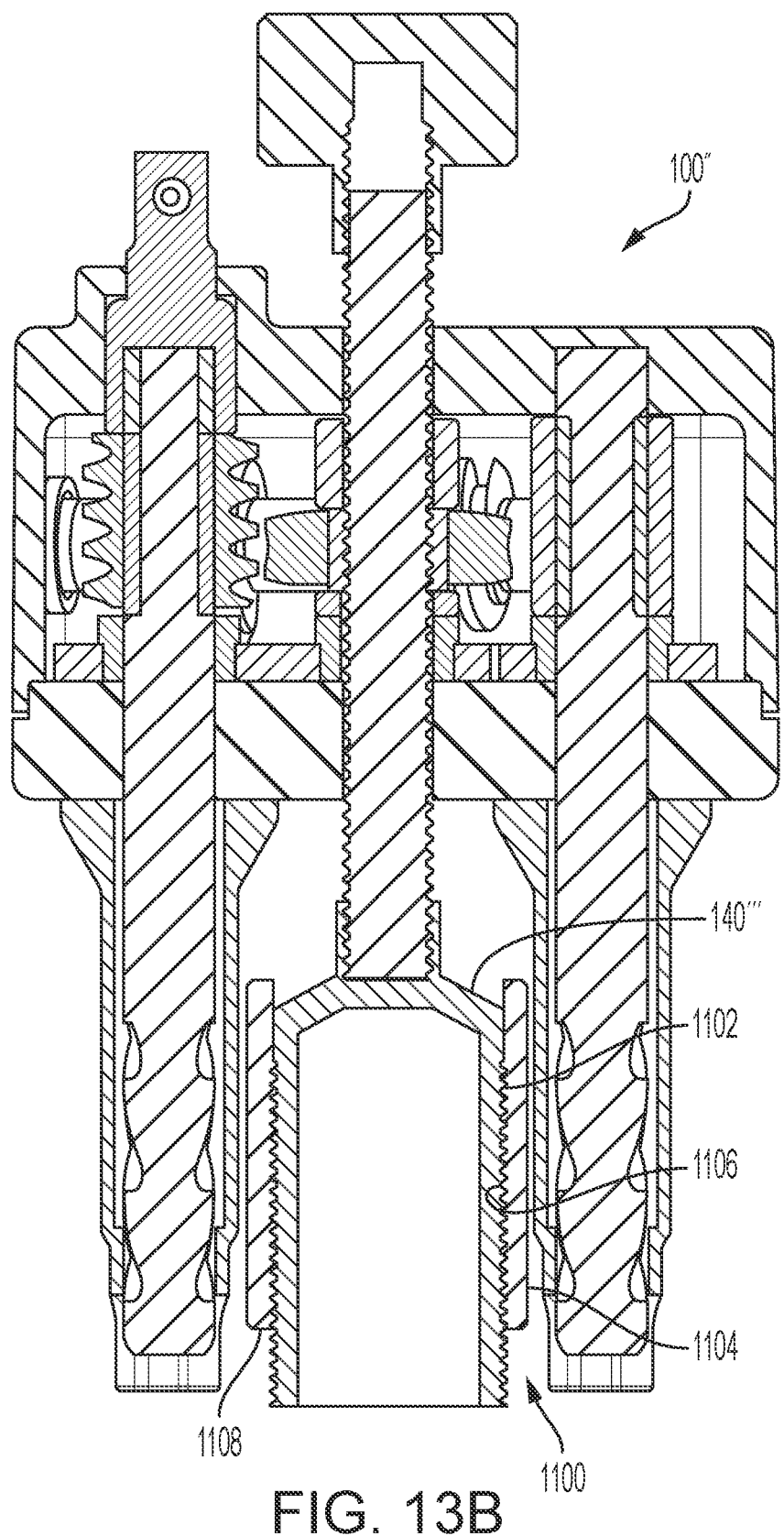
FIG. 13B is an elevational, cross-sectional view of the cutter of FIG. 13A for cutting an implant.

Referring to FIGS. 13A and 13B, there is shown another exemplary embodiment of a clamping mechanism 1100 operatively connected to the implant coupler 140'" for applying a clamping force to an unillustrated implant during cutting thereof. As shown in FIG. 13B, a circumferential surface of the implant coupler is externally threaded 1102. The clamping mechanism includes a substantially cylindrical sleeve 1104 surrounding the implant coupler and having internal threading 1106 configured to threadedly engage the external threading of the implant coupler. In addition, the internally threaded sleeve 1104 includes a distal edge 1108 operable to clampingly engage the implant. As shown in FIG. 13A, the external surface of the sleeve 1104 can be provided with structure 1110 for enhancing a user's grip when turning the sleeve relative to the implant coupler. Such structure can include recesses, raised ridges, knurling, and the like. Once the implant coupler is engaged with an implant (not illustrated), a user turns the sleeve 1104 in a direction to advance the distal edge 1108 of the sleeve into firm compressive engagement with the implant. The sleeve is locked in position by the application of sufficient torque upon engagement with the implant. With the implant firmly engaged, the milling operation is performed with minimal or no vibration of the implant occurring during milling, whereby the implant is easily and precisely cut by the implant cutter 100".

It will be appreciated by those skilled in the art that changes could be made to the exemplary embodiments described above without departing from the broad inventive concept thereof. It is to be understood, therefore, that this disclosure is not limited to the particular exemplary embodiments disclosed, but it is intended to cover modifications within the spirit and scope of the claims defined herein.

We claim:

1. A cutter for cutting an implant, comprising:
   a gearbox;
   a primary milling bit, a secondary milling bit and a lead screw operatively coupled to the gearbox;
   an input coupling coupled to the primary milling bit; and
   an implant coupler coupled to the lead screw,
   wherein the gearbox is operable to translate with respect to the lead screw and to drive the secondary milling bit in response to a driving force applied to the input coupling.

2. The cutter of claim 1, wherein the gearbox comprises:
   a translation drive assembly operable to translate the gearbox with respect to the lead screw in response to the driving force applied to the input coupling; and
   a milling drive assembly operable to drive the secondary milling bit in response to the driving force applied to the input coupling.

3. The cutter of claim 2, wherein the translation drive assembly comprises:
   a first worm screw circumscribing and coupled to the primary milling bit;
   a first worm gear operatively coupled to the first worm screw;

a second worm screw coupled rigidly to the first worm gear; and a second worm gear operatively coupled to the second worm screw, the second worm gear circumscribing the lead screw and having a socket.

4. The cutter of claim 3, wherein the translation drive assembly further comprises a nut in the socket of the second worm gear and threadedly engages the lead screw.

5. The cutter of claim 2, wherein the milling drive assembly comprises:

a first spur gear circumscribing and coupled rigidly to the primary milling bit;

a second spur gear operatively coupled to the first spur gear; and a third spur gear operatively coupled to the second spur gear and circumscribing and coupled rigidly to the secondary milling bit.

6. The cutter of claim 5, wherein the first, second and third spur gears are sized similarly, and each of the first, second and third spur gears each includes a same number of teeth.

7. The cutter of claim 1, further comprising first and second chip collectors coupled to the gearbox and respectively circumscribing the primary and secondary milling bits.

8. The cutter of claim 7, wherein each of the first and second chip collectors includes a cutout for receiving the implant and a chip collection cavity for maintaining chips and fragments milled from the implant.

9. The cutter of claim 8, wherein each of the first and second chip collectors includes a longitudinal guide rail to slidably engage with a respective groove on the implant coupler.

10. The cutter of claim 1, wherein the implant coupler includes a receptacle coupled to a distal end of the lead screw and a helicopter socket structured to releasably couple to the implant.

11. The cutter of claim 10, wherein the implant coupler includes a recess for receiving a tulip of a screw.

12. The cutter of claim 1, wherein each of the primary and secondary milling bits includes a distal cutting end with spiral flutes for cutting the implant and a proximal driving end operatively coupled to the gearbox.

13. The cutter of claim 12, wherein each of the distal cutting ends includes rounded edges.

14. The cutter of claim 1, wherein each of the primary and secondary milling bits comprise tungsten carbide.

15. The cutter of claim 1, wherein the primary milling bit, the secondary milling bit and the lead screw are spaced apart along a substantially linear path.

16. The cutter of claim 1, wherein the implant coupler is structured to couple to a spine rod.

17. The cutter of claim 1, wherein the input coupling is operable to receive a rotational driving force.

18. The cutter of claim 1, further comprising a clamping mechanism for applying a clamping force to an implant during cutting of the implant.

19. The cutter of claim 18, wherein the clamping mechanism comprises an axially extending shaft engaging the implant coupler, the shaft including a proximal end and an implant engageable tip at a distal end thereof operable to clampingly engage the implant.

20. The cutter of claim 18, wherein the clamping mechanism comprises a set screw extending through the implant coupler.

21. The cutter of claim 18, wherein the clamping mechanism comprises internal threads operable to threadedly engage the implant coupler, and a distal edge for clampingly engaging the implant.

22. A cutter for cutting a spine rod affixed to a spine, the cutter comprising:

a gearbox having a distal end, a translation drive assembly, and a milling drive assembly;

a primary milling bit having a proximal drive end operatively coupled to the translation and milling drive assemblies and a distal cutting end;

a secondary milling bit having a proximal drive end operatively coupled to the milling drive assembly and a distal cutting end for cutting the spine rod;

a lead screw operatively coupled to the translation drive assembly and having proximal and distal ends;

an input coupling coupled rigidly to the proximal drive end of the primary milling bit;

first and second chip collectors coupled to the distal end of the gearbox and respectively circumscribing the primary and secondary milling bits, each of the chip collectors including a cutout for receiving the spine rod, a chip collection cavity for maintaining chips and fragments cut from the spine rod, and an outer surface having a longitudinally disposed guide rail; and an implant coupler having a proximal receptacle coupled rigidly to the distal end of the lead screw, first and second grooves sized to respectively and slidably engage with the guide rails of the first and second chip collectors, and a distal end having a socket structured to releasably couple to the spine rod.

23. The cutter of claim 22, wherein the socket includes at least one receipt channel and at least one locking channel.

24. The cutter of claim 22, wherein a longitudinal axis of the primary milling bit and a longitudinal axis of the secondary milling bit are substantially parallel to a longitudinal axis of the lead screw.

* * * * *